(12) United States Patent
Beals et al.

(10) Patent No.: US 8,148,326 B2
(45) Date of Patent: *Apr. 3, 2012

(54) FLOWABLE CARRIER MATRIX AND METHODS FOR DELIVERING TO A PATIENT

(75) Inventors: Neil B. Beals, Memphis, TN (US);
Jeffrey L. Scifert, Arlington, TN (US);
Scott D. Boden, Atlanta, GA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 252 days.

This patent is subject to a terminal disclaimer.

(21) Appl. No.: 12/635,289

(22) Filed: Dec. 10, 2009

(65) Prior Publication Data

US 2010/0086600 A1 Apr. 8, 2010

Related U.S. Application Data

(63) Continuation of application No. 11/504,363, filed on Aug. 14, 2006, now Pat. No. 7,671,014.

(51) Int. Cl.
*A61K 38/00* (2006.01)
*A61K 38/16* (2006.01)
*A61K 38/17* (2006.01)
*A61K 38/18* (2006.01)
*A61K 38/39* (2006.01)

(52) U.S. Cl. ...... 514/8.8; 514/16.7; 514/16.8; 514/16.9; 514/17.1; 514/17.2

(58) Field of Classification Search .................. None
See application file for complete search history.

(56) References Cited

U.S. PATENT DOCUMENTS

| | | | |
|---|---|---|---|
| 4,925,924 A | 5/1990 | Silver et al. |
| 5,597,578 A | 1/1997 | Brown et al. |
| 5,677,284 A | 10/1997 | Li |
| 5,904,718 A | 5/1999 | Jefferies |
| 5,908,054 A | 6/1999 | Safabash et al. |
| 6,063,061 A | 5/2000 | Wallace et al. |
| 6,066,325 A | 5/2000 | Wallace et al. |
| 6,328,765 B1 | 12/2001 | Hardwick et al. |
| 6,780,192 B2 | 8/2004 | McKay et al. |
| 2001/0016703 A1 | 8/2001 | Wironen et al. |
| 2002/0106411 A1 | 8/2002 | Wironen et al. |
| 2002/0153632 A1 | 10/2002 | Schaufler |
| 2005/0112091 A1 | 5/2005 | DiMauro et al. |
| 2006/0029591 A1 | 2/2006 | Vukicevic et al. |
| 2006/0105042 A1 | 5/2006 | McKerracher |

FOREIGN PATENT DOCUMENTS

| | | |
|---|---|---|
| EP | 1025871 A1 | 8/2000 |
| WO | 9103491 A1 | 3/1991 |
| WO | 0124842 A2 | 4/2001 |
| WO | 0170288 A3 | 9/2001 |
| WO | 0178685 A1 | 10/2001 |
| WO | 03066083 A1 | 8/2003 |

*Primary Examiner* — Elizabeth C Kemmerer

(57) ABSTRACT

A carrier matrix may be delivered to a target position within a patient in a minimally invasive manner by first cutting a collagen sponge sheet into a plurality of relatively small pieces. These pieces are sized so that, when wet, they are capable of flowing through a cannula and/or reduced-diameter syringe tip. The pieces are placed into a syringe and wetted, say with a morphogenic solution, and optionally mixed with a bulking material, which is similarly sized to fit through the cannula. The thoroughly mixed and wetted product forms a viscous aggregate which may then be injected into the patient at the target site.

13 Claims, 7 Drawing Sheets

FLOWABLE CARRIER MATRIX AND METHODS FOR DELIVERING TO A PATIENT

FIELD OF THE INVENTION

The present invention relates to implantable medical devices for bone-related ailments. More particularly, the present invention discloses a method and related kit for providing a flowable carrier matrix that may be injected into a target site.

BACKGROUND OF THE INVENTION

The use of carrier matrices to promote the formation of bone at a site in a patient is well known, and related products are currently available on the market, such as MASTERGRAFT® Matrix, by Medtronic Sofamor Danek (Memphis, Tenn.). These matrices are typically in the form of a relatively large, soft collagen sponge. Before insertion into the target site, the sponge is wetted, usually with bone marrow aspirated from the patient, at a ratio of about 1:1 by volume. The bone marrow is permitted to soak into the scaffolding provided by the sponge, and the sponge is then kneaded by hand, thereby obtaining a pliable consistency that may subsequently be gently packed into the target site. The collagen in the sponge provides a malleable, non-water soluble carrier that permits accurate placement and retention of biological factors at the implantation site.

Because the sponge must be hand-packed, the surgeon is required to make an incision in the patient to reach the surrounding bone at the target site. The entire process is thus relatively invasive and painful. It would be beneficial if less intrusive means were available to deliver a collagen-based carrier matrix into a target space.

SUMMARY OF THE INVENTION

One aspect of the invention provides a method for delivering a carrier matrix to a target site, which comprises wetting a plurality of carrier matrix components with a fluid to create a viscous aggregate, and then injecting the viscous aggregate into the target site. The carrier matrix components comprise collagen, and in a specific embodiment are formed from collagen sponge, ranging from 1.0 mm to 10 mm in size. In certain embodiments the fluid comprises a morphogen. In other embodiments, the carrier matrix components are pre-impregnated with the morphogen. Additionally, a bulking material may be added to the viscous aggregate.

Another aspect provides a medical kit for practicing the above method. The medical kit comprises a plurality of carrier matrix components, a delivery system and a morphogen. In certain embodiments, the carrier matrix components are made from collagen sponge, and are no greater than 10 mm in size, nor less than 1.0 mm in size. The kit may further include a bulking material. The kit may also include a fluid transfer tube for connecting two syringes together to provide for the mixing together of the various components within the kit. In other embodiments, the delivery system includes a delivery cannula that is adapted to help with the injection of the viscous aggregate into the target site.

DETAILED DESCRIPTION

In the following, it should be understood that terms such as "include" or "comprise" are meant to indicate an inclusive, rather than an exclusive, listing of items. Items not indicated could be further included within such a list. Therefore, unless otherwise noted, exemplary lists of compounds or devices should not be construed as limiting; instead, it should be understood that such lists admit to additional, suitable items not explicitly indicated.

Figure 1:
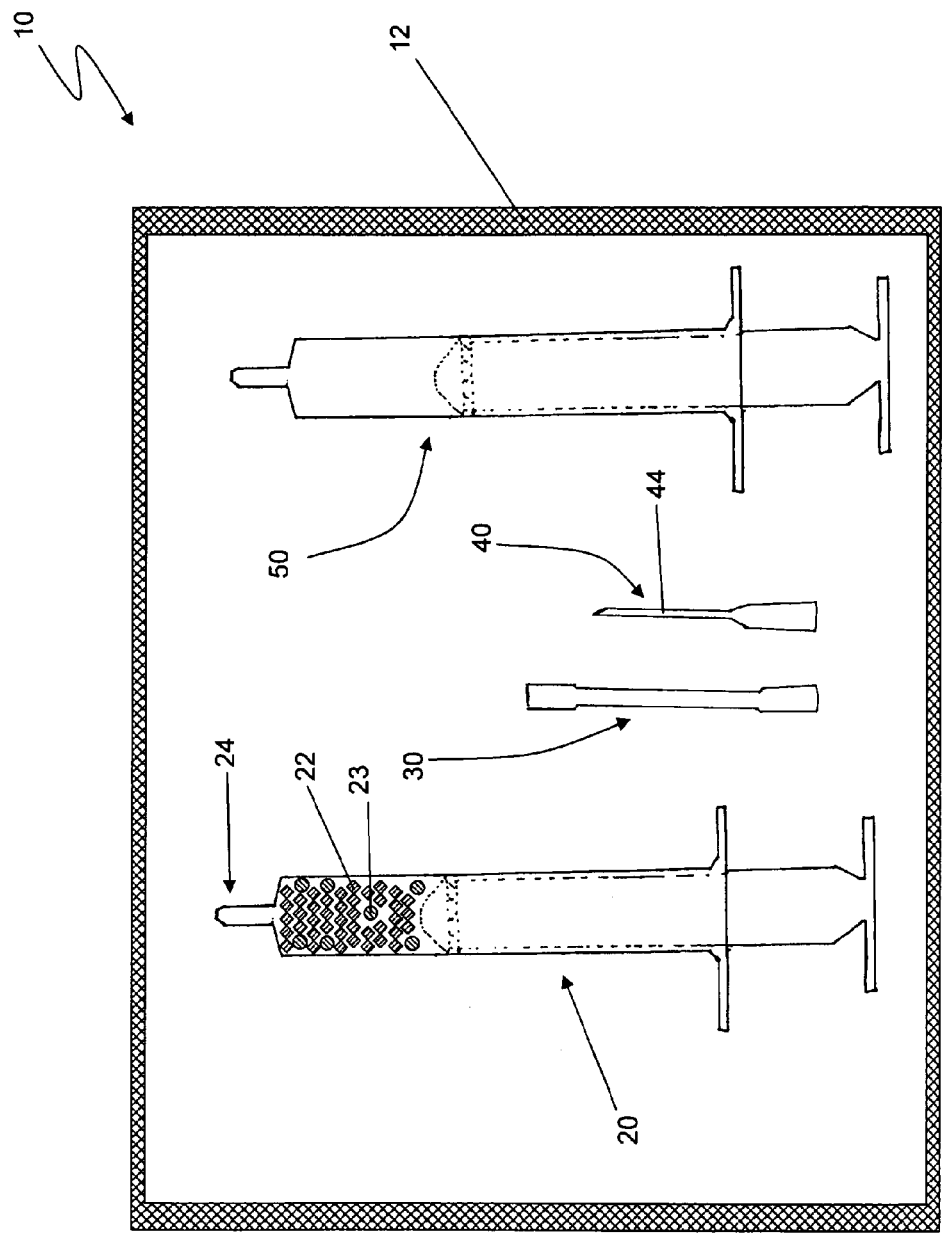
FIG. 1 depicts a first embodiment kit.

Reference is drawn to FIG. 1, which depicts a first embodiment kit 10. The kit 10 includes a first syringe 20, a fluid transfer tube 30, a delivery cannula 40 and a second syringe 50, all hermetically sealed within a sterile container 12. The components in the kit 10 are sterilized and remain packed within the container 12 until required for use. Appropriate sterilization and packing methods, as known in the art, may be used to prepare the kit 10. The kit 10 further includes a plurality of dry, collagen-comprising carrier matrix components 22. These components 22 may be packed in their own container, or, as shown in the specific embodiment of kit 10, the first syringe 20 may be loaded with the carrier matrix components 22. The distal end 24 of the first syringe 20 may be capped by any known manner to prevent loss of the matrix components 22 during handling of the kit 10. Although not shown, the kit 10 may also include an instruction sheet or sheets indicating the proper usage of the kit 10. The syringes 20, 50, and the delivery cannula 40 together form a delivery system that may be used to inject the instant invention flowable carrier matrix into a target site.

In the following, the term "carrier matrix" refers to collagen-comprising biomaterials for the orthopedic implant market which, when placed in a bone defect, provide scaffolding around which the patient's new bone will grow, gradually replacing the carrier matrix as the target site heals. Examples of suitable carrier matrices may include, but are not limited to, the MASTERGRAFT® Matrix produced by Medtronic Sofamer Danek, Inc., Memphis Tenn.; MASTERGRAFT® Putty produced by Medtronic Sofamer Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. HEALOS® marketed by Johnson & Johnson, USA; collagen sponges, e.g. HEMOSTAGENE® marketed by Coletica S A, France, or e.g. HELISAT® marketed by Integra Life Sciences Inc., USA; and COLLAGRAFT® Bone Graft Matrix produced by Zimmer Holdings, Inc., Warsaw, Ind.

The carrier matrix components 22 are small to moderately sized pieces of any suitable, collagen-comprising carrier matrix, with collagen sponge being the preferred carrier matrix for the components 22 due to its characteristics of being slick, pliable, yet mutually cohesive when wetted. Because the carrier matrix components 22 are subsequently injected via a cannula 44 into the target site, the size of the components 22 must be small enough to permit a fluid-like flow through the cannula 44. It is therefore expected that the size of any carrier matrix component 22 should not extend beyond 10 mm along any axis, with smaller sizes being required for smaller-gauged (i.e., thinner) cannulas 44. That is, the dimensions of the carrier matrix components 22 may depend upon the gauge of the cannula 44 that is subsequently used to inject them into the target site; this, in turn, may depend upon the morphology and pathology of the target site.

For example, within the kit 10, the carrier matrix components 22 may be in the form of pieces of dry collagen sponge 22, each about 5×5×2 mm in size, which would be suitable for later injection by a cannula 44 of at least gauge 16-21. It should be understood that the specific shape of the carrier matrix components 22 is less important than their actual dimensions along any axis; that is, the carrier matrix components 22 may be any shape, rectangular, circular, spherical, irregular or the like. However, it is further expected that the carrier matrix components 22 should not be so small as to make them likely to flow away from the target site if placed under minimal pressure. It is believed that the carrier matrix components 22 are ideally at least 1.0 mm in size. Performance constraints may therefore be placed on the size of the carrier matrix components 22, in which size is determined by the delivery system, such as the gauge of the delivery cannula 44, and/or the limitations of the surgical space; the posterolateral spine, for example, may necessitate a larger, more cohesive mass of carrier matrix components 22 in order to resist soft-tissue compression, while a more enclosed, load-protected space may allow for smaller-sized components 22 of the viscous aggregate matrix to be used effectively.

In certain beneficial embodiments, the components 22 of the composition will be randomly or regularly shaped sponge pieces. These sponge pieces can be prepared as individual pieces or by fragmentation of one or more larger sponge structures. The sponge pieces can each exhibit a porous structure and can each exhibit a compressible or otherwise deformable character with complete or partial shape memory. In this manner, beneficial space-filling properties can be imparted to the overall viscous aggregate which, upon implantation, can deform and/or expand to occupy the volume desired for bone ingrowth. Further, the sponge pieces can be chemically crosslinked materials, for example crosslinked with an aldehyde crosslinker such as formaldehyde or glutaraldehyde, or another suitable chemical crosslinker such as a carbodiimide, or by other techniques such as dehydrothermal or radiation-induced crosslinking. Such crosslinking can serve to provide scaffolding material for bone ingrowth that has increased persistence at an implant site relative to a corresponding non-crosslinked material.

Although the specific embodiment kit 10 depicts the use of a separate delivery cannula 40 as part of a delivery system, it will be appreciated that the distal end 24 of the syringe 20 may simply be extended to provide a suitable delivery system for the present invention. Hence, it should be understood that the cannula 44 through which the viscous aggregate of the carrier matrix components 22 will be injected into the target site may by either detachably connected to the syringe 20 in a known manner, or may simply be an integral part of the syringe 20.

The kit 10 further comprises a morphogen. Generally, the morphogen may be in a dry form, within its own container or the second syringe 50, for later reconstitution as known in the art. Alternatively, the morphogen may be in a liquid form and stored in the second syringe 50 or in its own vial; or, as in the specific embodiment for the kit 10, the carrier matrix components 22 can be packaged pre-impregnated with the morphogen. The term "morphogen" refers to any factor that stimulates or induces bone growth. Example morphogens include, but are not limited to, Bone Morphogenetic Proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βs), including TGF-β-1, TGF-β-2, and TGF-β-3, and inhibitors for tumor necrosis factor (e.g., anti-TNFα). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, which is incorporated herein by reference. The polynucleotides encoding the same may also be administered as gene therapy agents. The preferred morphogens are the recombinant human bone morphogenetic proteins (rhBMPs) because they are available in relatively unlimited supply and do not transmit infectious diseases. Most preferably, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al.

The kit 10 may further include one or more other bioactive agents. These bioactive agents may be mixed in with the morphogen, provided separately, impregnated within the carrier matrix components 22, or the like. The bioactive agent or agents may include, but are not limited to, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, osteoinductive factors, anti-arthritics, and diagnostic agents.

A bulking material 23 may also be provided within the kit 10. This bulking material 23 may be provided in its own container, in either of the syringes 20, 50, or mixed with or impregnated into the carrier matrix components 22. The bulking material 23 is a material that is added to the carrier matrix components 22 to provide limited compression-resistance and stiffness to the carrier matrix provided by the viscous aggregate. The bulking material 23 should have a particle size that is sufficiently small to flow through the delivery cannula 44. Exemplary bulking materials include collagen/ceramic combination products; allograft; and bio-compatible ceramics or minerals that provide a scaffold for bone ingrowth. The ceramics or minerals may be either natural or synthetic, and may include, for example, bone particles, BIOGLASS®, tricalcium phosphate, biphasic calcium phosphate, hydroxyapatite, or corraline hydroxyapatite. Biphasic calcium phosphate may be a particularly desirable synthetic ceramic for use in the kit 10.

Figure 2:
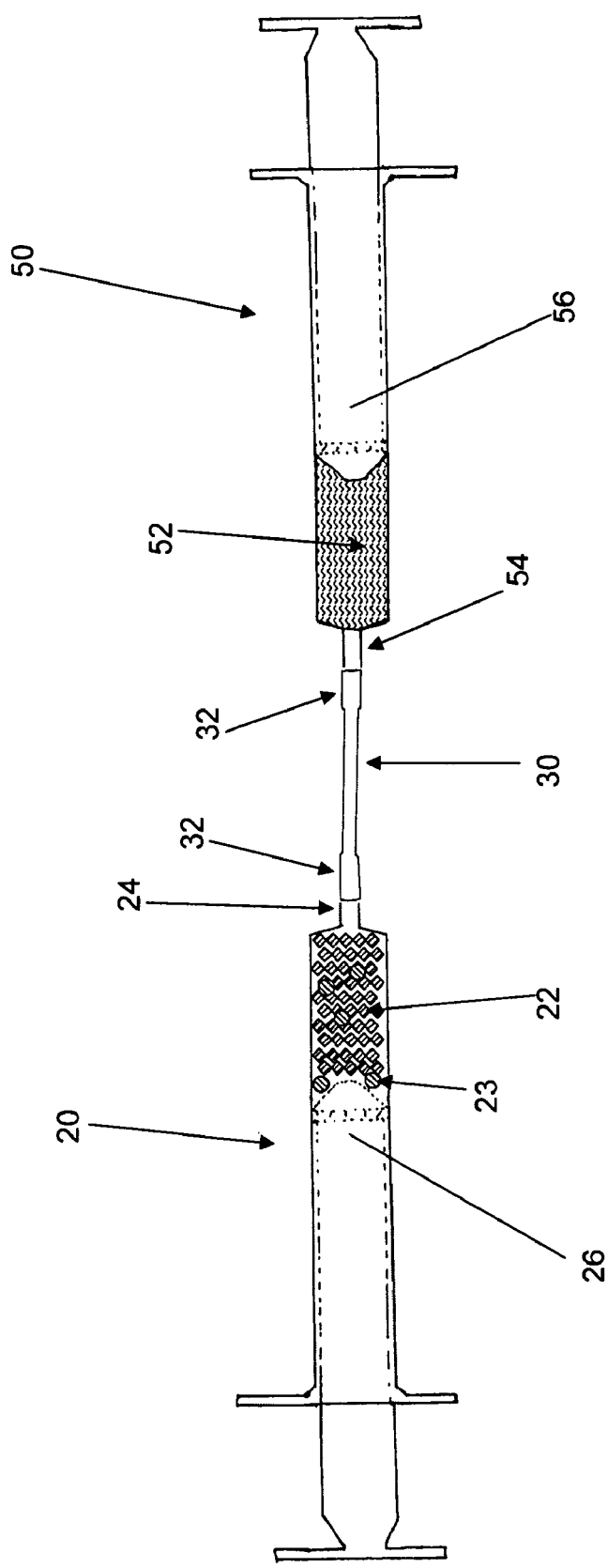
FIGS. 2 to 4 illustrate using the kit shown in FIG. 1 to create a flowable carrier matrix.

The kit 10 provides many of the tools needed to permit a surgeon to practice the method of the present invention. The invention method comprises wetting a plurality of carrier matrix components with a fluid, thereby forming a viscous aggregate, and then injecting the resultant viscous aggregate into the target site. The viscous aggregate is a flowable material, and hence forms a flowable carrier matrix. To this end, as shown in FIG. 2, the first syringe 20 and second syringe 50 may be removed from the packaging 12, and the second syringe 50 may be loaded with a suitable amount of a suitable fluid 52, such as distilled water, aspirated bone marrow, or the like. The amount of fluid 52 used in the second syringe 50 will correspond to the amount of carrier matrix 22 provided in the first syringe 20; volumetric ratios are typically about 1:1, carrier matrix to fluid. Hence, if, for example, the carrier matrix components 22 form 6 cc in total of collagen sponge, then about 6 ml of fluid should be loaded into the second syringe 50. However, it will be appreciated that the actual ratios used will depend upon the specific type of carrier matrix 22 employed, with greater and lesser ratios being possible. It will further be appreciated that the fluid 52 used to wet the carrier matrix components 22 is not limited to those listed above. On the contrary, solutions may be employed that contain one or more of any number of ingredients, such as salts, sugars, analgesics, anti-inflammatory substances, antibiotics, or any other biologically active substance, preservative, radiographic marker or excipient deemed necessary by the attending physician, including the bioactive agents listed above. This is particularly true if the morphogen is not already pre-impregnated within the carrier matrix components 22; in this case, then, the fluid 52 will contain the morphogen, as either reconstituted by the physician, or as provided in liquid form within the kit 10.

Figure 3:
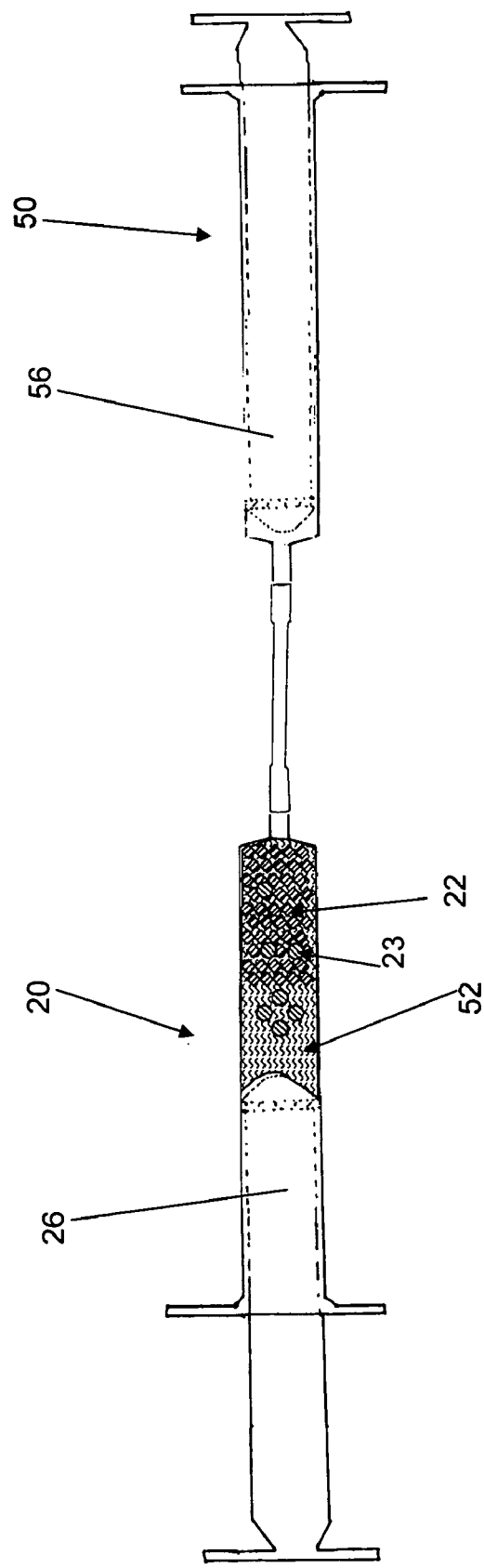
Figure 4:
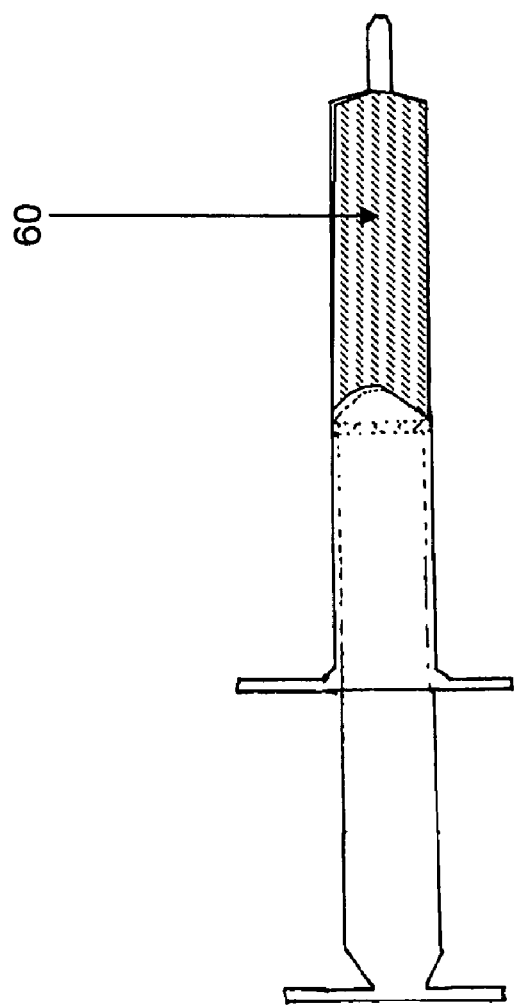

If the bulking material 23 is desired and is not already present within the carrier matrix components 22, then the bulking material 23 should be added to the carrier matrix components 22 within, for example, the first syringe 20. Then, the first syringe 20 and second syringe 50 may be fluidly connected to each other by way of the fluid transfer tube 30. The fluid transfer tube 30 is simply a tube with two ends 32 adapted to connect with the distal ends 24, 54 of the syringes 20, 50. Any standard mating arrangement commonly used for syringes may be employed, such as Luer-locks. Of course, the syringes 20, 50 may be designed to mate directly with each other, thus obviating the need of the fluid transfer tube 30. Once connected to the first syringe 20, the plunger 56 of the second syringe 50 may be depressed to inject the fluid 52 into the first syringe 20, as shown in FIG. 3. The fluid 52 thus wets the plurality of carrier matrix components 22. The fluid 52 may be permitted some time to soak into the carrier matrix components 22, typically for about 1 to 3 minutes, during which time the carrier matrix components 22 become soft and pliable, and absorb any bioactive components in the fluid 52, such as the morphogen or bioactive agent, if present. The carrier matrix components 22 may then by thoroughly blended together with the fluid 52, and with the optional bulking material 23, by repetitively operating the plungers 26 and 56 to drive the mixture back and forth between the syringes 20, 50. The result, as shown in FIG. 4, is a viscous aggregate 60, impregnated with the morphogen and optionally a bulking material and bioactive agent(s), inside either of the syringes 20, 50, which may then be injected into the target site within the patient.

Figure 5:
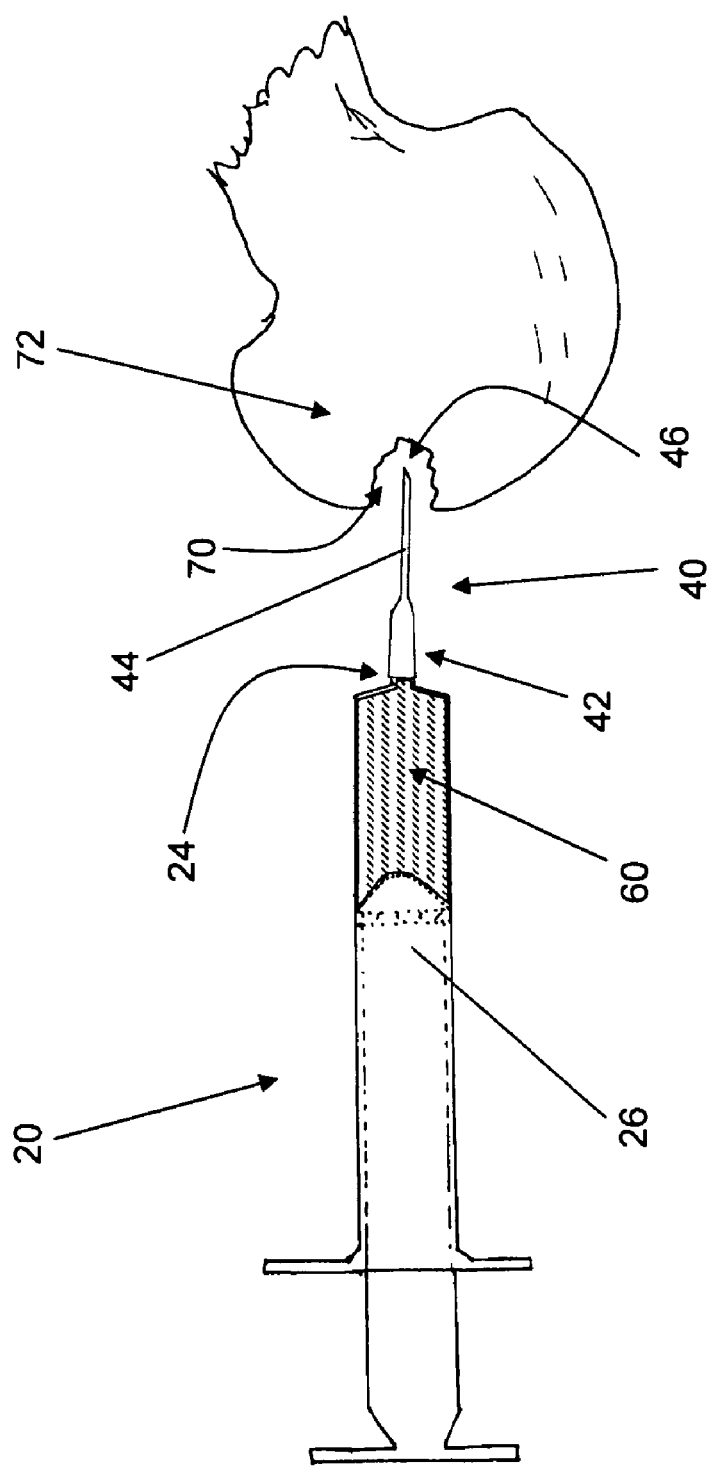
FIGS. 5 and 6 illustrate injecting a viscous aggregate into a target site.

In the following, the term "injection" indicates the placement of material at a target site by the extrusion of such material from the distal end of a cannula, tube, orifice or the like. If, for example, the viscous aggregate 60 is left in the first syringe 20, then, as shown in FIG. 5, the delivery cannula 40 may be attached to the syringe 20 to provide for injection of the viscous aggregate 60 into a target site 70 within a patient. As with the fluid transfer tube 30, the delivery cannula 40 contains a suitable mating element 42 on its proximal end that permits physical and fluidic connection of the delivery cannula with the distal end 24 of the syringe 20. As indicated earlier, a separate delivery cannula 40 is not a requirement of the delivery system. For example, the distal end 24 of the syringe 20 may simply be extended to provide a suitable injection device; indeed, even a standard syringe tip may be used as in injection device under certain conditions. By applying pressure on the plunger 26, the viscous aggregate 60 flows through the cannula 44, or equivalent device, to extrude from the distal end 46 into the target site 70. The target site 70 is typically a region in which structural support in the surrounding skeletal system 72 is not required, and may include, for example, both open and closed long bone fractures, as well as cages (as for spinal fusion), or oral maxillofacial applications, such as ridge augmentation. The length, diameter and distal end 46 of the delivery cannula 40 may all be adapted for the particular characteristics and requirements of both the target site 70 and the viscous aggregate 60. Alternatively, the kit 10 may be provided with a plurality of different types of delivery cannula members 40, each designed for a particular application, which the surgeon may then use as the particular situation warrants.

Compositions of the present invention can be used, for example, in the practice of minimally-invasive spinal fusion procedures, including those involving anterior surgical approaches, e.g. using laproscopic instrumentation, and those involving posterior surgical approaches, e.g. using introducer sleeves. Suitable Minimal Access Spinal Technology (MAST) products for these types of procedures are available, for example, from Medtronic Sofamor Danek, Inc. (Memphis, Tenn.), including for instance the METRX.™-X-TUBE™ retraction system.

Generally in minimally invasive approaches, surgical access is provided to the interbody space through a cannulated device (e.g. a laparoscope or sleeve). In one specific example, minimally invasive posterior access can be provided by a procedure that includes positioning of a cannulated device, such as the X-TUBE™, within soft patient tissues, e.g. after incision and passage of a series of tissue dilators of increasing size to create an opening for the cannulated device. Oftentimes, a laminectomy is performed, in which at least a portion of the lamina will be excised from a vertebra occurring above the disc space to be accessed. Potentially also, the procedure can involve excision of at least a portion of an articular facet (facetectomy) or other bony structures as necessary for surgical access. After access to the disc space is gained, patient disc tissue can be excised, the vertebral endplates can be decorticated using minimally invasive instrumentation therefor, and one or more loadbearing implants, such as cages or bone spacers, can optionally be introduced through the cannulated device. In accordance with certain embodiments described herein, the flowable carrier matrix combined with an osteogenic substance can be introduced into the disc space using a syringe or other cannulated device.

In certain aspects, osteogenic compositions as described herein can also be delivered to other surgical sites, particularly sites at which bone growth is desired. These include, for instance, the repair of cranial defects, iliac crest back-filling, acetabular defects, and in the repair of tibial plateau and long bone defects. Such methods can be used to treat major or minor defects in these or other bones caused by trauma (including open and closed fractures), disease, or cogenital defects, for example.

Figure 6:
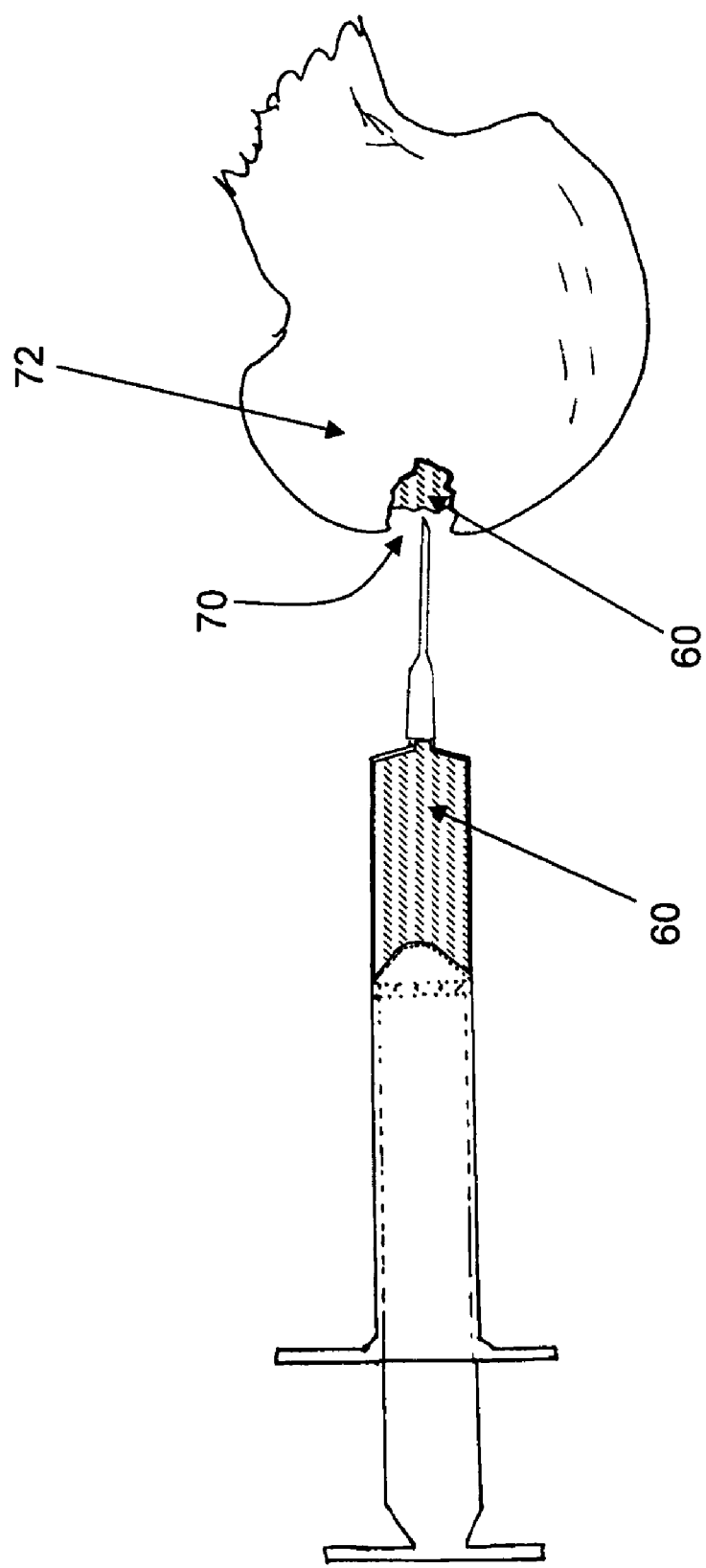

As shown in FIG. 6, when the viscous aggregate 60 is injected into the target site 70, the viscous aggregate 60 adheres both to itself and the bone 72 around the target site 70, thus filling the void in the bone 72 at the target site 70. As known in the art, the viscous aggregate 60 serves as scaffolding for bone cells, which grow into and absorb the matrix the viscous aggregate 60 provides, replacing the matrix with native bone 72. The presence of the morphogen and bulking material within the viscous aggregate 60 help to effectuate this process. Because the cannula 44 is used to inject the viscous aggregate 60 into the target site 70, there may be no, or at least reduced, need for incisions or the like to gain access to the target site 70. The present invention injection method thus provides a minimally invasive technique to deliver the viscous aggregate 60 to the target site 70. One of skill in the art will readily appreciate that, since the injection technique is minimally invasive, it may be desirable to provide a radiographic marker in the viscous aggregate 60 to assist in the imaging of the injection procedure. If present, the ceramic component within the viscous aggregate may provide a certain amount of radiopacity; however, additional radiopaque material may be added, such as barium beads. The radiopaque material may be included within the kit 10.

Figure 7:
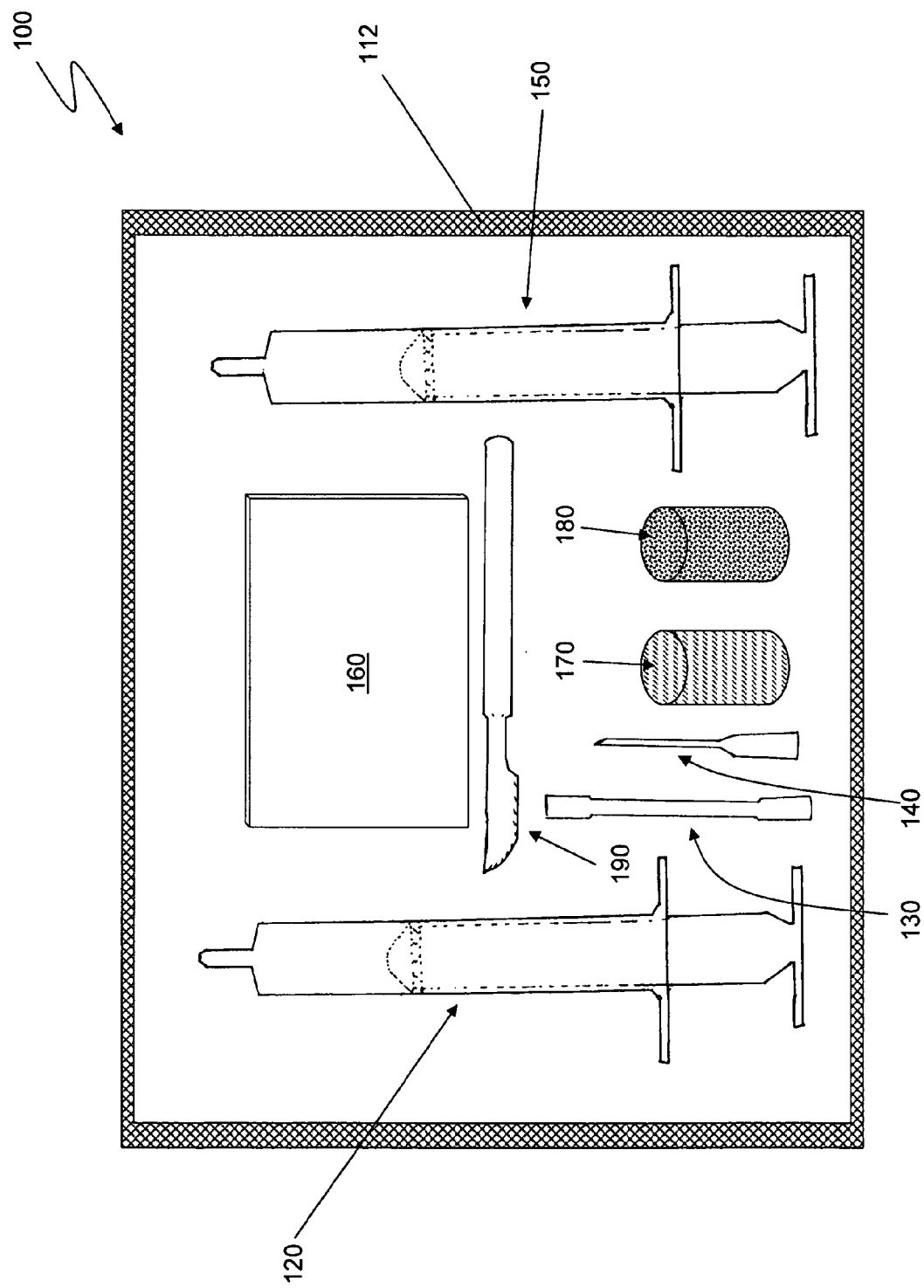
FIG. 7 depicts a second embodiment kit.

An alternative kit 100 is shown in FIG. 7. Rather than providing a plurality of carrier matrix components, the kit 100 provides a single sheet of a collagen-comprising carrier matrix, and means to cut this sheet into a plurality of carrier matrix components. The exemplary kit 100 includes a first syringe 120, a fluid transfer tube 130, a delivery cannula 140, a second syringe 150, a collagen-comprising carrier matrix sheet 160, morphogen 170, bulking material 180 and cutting means 190, all of which are hermetically sealed within a sterile container 112. The morphogen 170 may be in a dry form to be later reconstituted when needed, or may be in liquid form; the morphogen 170 could also be held in either of the syringes 120, 150. Similarly, the bulking material 180 could be stored in either of the syringes 120, 150, rather than packaged in its own container. The carrier matrix sheet 160 may be any suitable collagen-based carrier matrix, such as a collagen sponge. The cutting means 190 is provided to enable a physician to cut the carrier matrix sheet 160 into a plurality of small pieces, as carrier matrix components, that are suitably sized to be injectable through the delivery cannula 140. The cutting means 190 may be any suitable cutting device, such as a scalpel, scissors or the like. Once cut into the appropriately sized pieces, such as pieces less than 10 mm in size, the cut pieces of the carrier matrix 160 may be placed in the syringe 120, wet with a solution made from the morphogen 170, and then mixed with the bulking material, using the second syringe 150 and fluid delivery tube 130, as discussed above, to form a viscous aggregate. The resultant viscous aggregate may then be injected into a target site, using the delivery cannula 140.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method for delivering a carrier matrix to a target site within a patient, the method comprising:
    wetting a plurality of carrier matrix components with a fluid to create a viscous aggregate comprising BMP-2 and a bulking material selected from one or more of collagen-ceramic composite materials, allograft and bio-compatible ceramics or minerals that provide bone ingrowth scaffolding, wherein the carrier matrix components comprise solid collagen pieces ranging from about 1.0 mm to about 10 mm in size; and
    injecting the viscous aggregate into the target site, wherein the viscous aggregate is a flowable material.

2. The method of claim 1 wherein the viscous aggregate further comprises a bioactive agent selected from a set consisting of antimicrobials, antibiotics, antimyobacterial, antifungals, antivirals, antineoplastic agents, antitumor agents, agents affecting immune response, blood calcium regulators, agents adapted to regulate glucose, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, allergic response inhibitors, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, osteoinductive factors, antiarthritics, and diagnostic agents.

3. The method of claim 1 wherein the carrier matrix components are sized to permit a fluid-like flow through a delivery device used to inject the viscous aggregate into the target site.

4. A medical kit comprising:
    a plurality of carrier matrix components, the carrier matrix components comprising solid collagen pieces ranging from about 1.0 mm to about 10 mm in size;
    a bulking material selected from one or more of collagen-ceramic composite materials, allograft and bio-compatible ceramics or minerals that provide bone ingrowth scaffolding;
    a morphogen; and
    a delivery system for injecting into a site a viscous aggregate resulting after mixing together the carrier matrix components and the morphogen, wherein the morphogen is BMP-2 and the viscous aggregate is a flowable material.

5. The medical kit of claim 4 further comprising a bioactive agent selected from a set consisting of antimicrobials, antibiotics, antimyobacterial, antifungals, antivirals, antineoplastic agents, antitumor agents, agents affecting immune response, blood calcium regulators, agents adapted to regulate glucose, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, allergic response inhibitors, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, osteoinductive factors, antiarthritics, and diagnostic agents.

6. The medical kit of claim 4 further comprising a fluid delivery tube for fluidly connecting together at least two syringes.

7. The medical kit of claim 4 wherein the delivery system comprises two syringes that are fluidly connectable to each other.

8. The medical kit of claim 4 wherein the delivery system comprises at last least one delivery cannula to deliver the viscous aggregate to the site.

9. The medical kit of claim 4 wherein the carrier matrix components are sized to permit a fluid-like flow through a delivery device used to inject the viscous aggregate into the target site.

10. A method for promoting spinal fusion in a subject, comprising:
providing a flowable osteogenic composition comprising a plurality of solid collagen sponge pieces wetted with an osteogenic formulation to create a viscous aggregate comprising BMP-2 and a bulking material selected from one or more of collagen-ceramic composite materials, allograft and bio-compatible ceramics or minerals that provide bone ingrowth scaffolding, wherein the solid collagen sponge pieces range from about 1.0 mm to about 10 mm in size; and
passing said flowable osteogenic composition through a cannulated delivery device and into a location at which bone ingrowth is desired, said location between adjacent vertebrae in the subject.

11. The method of claim 10 wherein said location is between adjacent transverse processes of a spine of the subject.

12. The method of claim 10, wherein said location is in an interbody space between the adjacent vertebrae.

13. The method of claim 12, wherein said location is within a cavity defined by a load-bearing spinal implant in the interbody space.

* * * * *

UNITED STATES PATENT AND TRADEMARK OFFICE
CERTIFICATE OF CORRECTION

PATENT NO. : 8,148,326 B2  
APPLICATION NO. : 12/635289  
DATED : April 3, 2012  
INVENTOR(S) : Beals et al.

Page 1 of 1

It is certified that error appears in the above-identified patent and that said Letters Patent is hereby corrected as shown below:

In Column 4, Line 30, delete "antimyobacterial," and insert -- antimycobacterial, --, therefor.

In Column 4, Lines 35-36, delete "cholnergics," and insert -- cholinergics, --, therefor.

In Column 4, Line 41, delete "anorexigenlcs," and insert -- anorexigenics, --, therefor.

In Column 5, Line 13, delete "fluid" and insert -- fluid 52 --, therefor.

In Column 6, Lines 2-3, delete "cannula" and insert -- cannula 40 --, therefor.

In Column 6, Line 63, delete "cogenital" and insert -- congenital --, therefor.

In Column 8, Line 7, in Claim 2, delete "antimyobacterial," and insert -- antimycobacterial --, therefor.

In Column 8, Line 44, in Claim 5, delete "antimyobacterial," and insert -- antimycobacterial --, therefor.

Signed and Sealed this  
Twenty-eighth Day of August, 2012

David J. Kappos  
*Director of the United States Patent and Trademark Office*